United States Patent
Sawa et al.

(10) Patent No.: US 8,299,124 B2
(45) Date of Patent: Oct. 30, 2012

(54) AQUEOUS INTRAOCULAR PENETRATION-PROMOTING EYE DROP

(75) Inventors: Shirou Sawa, Kobe (JP); Tomoko Fujimoto, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/332,827

(22) Filed: Dec. 21, 2011

(65) Prior Publication Data

US 2012/0095101 A1    Apr. 19, 2012

Related U.S. Application Data

(62) Division of application No. 10/568,418, filed as application No. PCT/JP2005/020302 on Nov. 4, 2005, now abandoned.

(30) Foreign Application Priority Data

Nov. 5, 2004  (JP) .................................. 2004-322569

(51) Int. Cl.
    *A61K 31/19*    (2006.01)
    *A61K 31/04*    (2006.01)
(52) U.S. Cl. ......................... 514/568; 514/740; 514/912
(58) Field of Classification Search .................. 514/568, 514/740, 912
    See application file for complete search history.

(56) References Cited

U.S. PATENT DOCUMENTS

| | | | |
|---|---|---|---|
| 2,860,160 A * | 11/1958 | Sundberg et al. ............... | 562/44 |
| 4,563,291 A | 1/1986 | Penny | |
| 4,829,083 A | 5/1989 | Doulakas | |
| 4,829,088 A | 5/1989 | Doulakas | |
| 4,910,225 A | 3/1990 | Ogawa et al. | |
| 5,603,929 A | 2/1997 | Desai et al. | |
| 5,653,972 A | 8/1997 | Desai et al. | |
| 5,849,291 A | 12/1998 | Kessler | |
| 5,945,121 A | 8/1999 | Kato et al. | |
| 6,281,224 B1 | 8/2001 | Miyagi et al. | |
| 6,335,335 B2 | 1/2002 | Higashiyama et al. | |
| 2004/0120916 A1 | 6/2004 | Huth | |
| 2005/0239895 A1 | 10/2005 | Sawa et al. | |

FOREIGN PATENT DOCUMENTS

| | | |
|---|---|---|
| EP | 0 243 308 | 10/1987 |
| EP | 1 683 526 | 7/2006 |
| JP | 59-89616 | 5/1984 |
| JP | 61-12617 | 1/1986 |
| JP | 62-242617 | 10/1987 |
| JP | 62-242618 | 10/1987 |
| JP | 59-89617 | 12/1988 |
| JP | 63-301822 | 12/1988 |
| JP | 2-124817 | 5/1990 |
| JP | 8-291065 | 11/1996 |
| JP | 11-335301 | 12/1999 |
| JP | 2002-114711 | 4/2002 |
| WO | 96/19211 | 6/1996 |
| WO | 99/22715 | 5/1999 |
| WO | 2004/064828 | 8/2004 |
| WO | 2005/046700 | 5/2005 |

OTHER PUBLICATIONS

Point Cross, Partition Coefficient, 2009, printed from http://www1.pointcross.com/source/ddg/steps/preclinical/preformulation/Partition_coefficient/index.html, 2 pages.*
English translation of the International Preliminary Examination Report and Written Opinion issued May 8, 2007 in International (PCT) Application No. PCT/JP2005/020302.
H. Sasaki et al., "Different Effects of Absorption Promoters on Corneal and Conjunctival Penetration of Ophthalmic Beta-Blockers", Pharmaceutical Research, vol. 12, No. 8, pp. 1146-1150, 1995.
H. Sasaki et al., "Ophthalmic Preservatives as Absorption Promoters for Ocular Drug Delivery", J. Pharm. Pharmacol., vol. 47, pp. 703-707, 1995.
Supplementary Partial European Search Report dated Feb. 7, 2008 in corresponding European Application No. 05805529.
Endo et al., Mechanisms of Cytoprotective Effect of Amino Acids on Local Toxicity Caused by Sodium Laurate, a Drug Absorption Enhancer, in Intestinal Epithelium, Mar. 2002, Journal of Pharmaceutical Sciences, vol. 91, No. 3, pp. 730-743.
Ogawa et al., Effects of bromfenac sodium, nonsteroidal anti-inflammatory drug, on acute ocular inflammation, 1995, Nippon Ganka Gakkai Zasshi, 99(4):406-11 (Abstract only) printed from http://www.ncbi.nlm.nih.gov/pubmed/7741052 on Jun. 10, 2009.
Baudouin, Dry Eye: An Unexpected Inflammatory Disease, Apr. 2001, Archivos de la Sociedad Espanola de Oftalmologia, No. 4, printed from http://www.oftalmo.com/seo/archivos/maquetas/E/28CB7243-EAFA-2FE8-823F-000047B616CE/articulo.html, 1 page.
Lobefal et al., Dry eye in allergic conjunctivitis: role of inflammatory infiltrate, Int J Immunopathol Pharmacol. Jan.-Apr. 1999;12(3), Abstract only, printed from http://www.ncbi.nlm.nih.gov/pubmed/12783641, 1 page.
Leike et al., Effects of Compound Taurine Eye Drops on Ocular Inflammation in Rabbits, Chinese Ophthalmic Research, 1997, printed from http://encnki.com.cn/Article_en/CJFDTOTAL-YKYJ703.012.htm, 2 pages, Abstract only.

* cited by examiner

*Primary Examiner* — Sreeni Padmanabhan
*Assistant Examiner* — Gigi Huang
(74) *Attorney, Agent, or Firm* — Wenderoth, Lind & Ponack, L.L.P.

(57) ABSTRACT

An aqueous eye drop comprising 2-amino-3-(4-bromobenzoyl)phenylacetic acid or its pharmacologically acceptable salt or a hydrate thereof and an organic amine (for example, aminoethylsulfonic acid or trometamol) or a salt thereof is useful as an eye drop for once a day administration for treating inflammatory diseases of the external segment or the anterior segment of the eyes, since such aqueous eye drop can maintain a therapeutically effective concentration of 2-amino-3-(4-bromobenzoyl)phenylacetic acid in anterior aqueous humor for at least 24 hours by once a day administration.

4 Claims, No Drawings

AQUEOUS INTRAOCULAR PENETRATION-PROMOTING EYE DROP

This application is a divisional application of U.S. application Ser. No. 10/568,418, filed Apr. 26, 2006, now abandoned which is the national phase filing of International Patent Application No. PCT/JP2005/020302, filed Nov. 4, 2005.

TECHNICAL FIELD

The present invention relates to an aqueous eye drop which is administered once a day, comprising an anti-inflammatory, 2-amino-3-(4-bromobenzoyl)phenylacetic acid or its pharmacologically acceptable salt thereof or a hydrate thereof as an active ingredient, and having a promoted intraocular penetration and a prolonged retention time of a concentration of 2-amino-3-(4-bromobenzoyl)phenylacetic acid penetrated into the anterior aqueous humor.

The present invention also relates to a method for promoting an intraocular penetration of 2-amino-3-(4-bromobenzoyl)phenylacetic acid or its pharmacologically acceptable salt thereof or a hydrate thereof, and prolonging a retention time of a concentration of 2-amino-3-(4-bromobenzoyl)phenylacetic acid penetrated into the anterior aqueous humor, characterized in that an organic amine or its salt is combined with an aqueous eye drop comprising, as an active ingredient, 2-amino-3-(4-bromobenzoyl)phenylacetic acid or its pharmacologically acceptable salt or a hydrate thereof.

BACKGROUND ART

2-Amino-3-(4-bromobenzoyl)phenylacetic acid (generic name: bromfenac) is a compound represented by the following formula (I) and is an acidic non-steroidal anti-inflammatory agent.

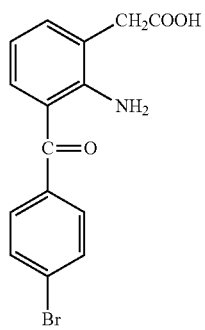

(I)

2-Amino-3-(4-bromobenzoyl)phenylacetic acid or its pharmacologically acceptable salt or a hydrate thereof is effective for inflammatory diseases of the external segment and the anterior segment of the eyes (for example, uveitis, blepharitis, conjunctivitis, scleritis, and postoperative inflammation, etc.). Particularly, efficacy of such compound for treating uveitis is comparable with steroidal anti-inflammatory agents which have been conventionally used therefor (JP-2-124817-A (U.S. Pat. No. 2,683,676)). 2-Amino-3-(4-bromobenzoyl)phenylacetic acid or its pharmacologically acceptable salt or a hydrate thereof has been put into practical use in the form of an eye drop as sodium salt and 3/2 hydrate in the field of ophthalmology.

Meanwhile, an eye drop having an improved intraocular penetration and intraocular retention of medicaments has been desired in the field of ophthalmology. However, improvement of intraocular penetration and intraocular retention, etc. has not been previously reported on 2-amino-3-(4-bromobenzoyl)phenylacetic acid or its pharmacologically acceptable salt or a hydrate thereof.

With respect to administration to the eyes, examples of medicaments having improvement in absorption promotion into an ocular tissue or intraocular retention include, for example, the followings: H. Sasaki et al., Pharmaceutical Research, 1995, vol. 2, no. 8, p. 1146-1150, discloses that corneal permeability of β-blockers such as atenolol, carteolol, tilisolol, and timolol was accelerated by capric acid in an in vitro experiment; WO 99/22715 discloses that a $C_3$-$C_7$ fatty acid prolonged a retention time of β-blocker in the ocular tissue; and JP-A-63-301822 (U.S. Pat. No. 2,563,336) discloses that a combination of caproic acid, caprylic acid, and capric acid improved corneal permeability of bunazosin hydrochloride which is an $\alpha_1$ adrenergic receptor blocker. In addition, it is also reported that benzalkonium chloride used as antiseptic in an eye drop promotes not only corneal permeability of tilisolol and FITC (fluorescein isothiocyanate)-dextran but also conjunctival permeability thereof slightly in H. Sasaki et al., Journal of Pharmacy and Pharmacology, 1995, vol. 47, no. 9, p. 703-707).

However, in these prior literatures, there is no descriptions with respect to a method for promoting the penetration of 2-amino-3-(4-bromobenzoyl)phenylacetic acid or its pharmacologically acceptable salt or a hydrate thereof into the ocular tissue, and for retaining an effective concentration of 2-amino-3-(4-bromobenzoyl)phenylacetic acid in the anterior aqueous humor for treating inflammatory diseases.

Meanwhile, an organic amine such as trometamol and the like is used as a buffer in the field of ophthalmology. In addition, the organic amine such as trometamol and the like is used for stabilization, solubilization, reduction of irritation, and improvement of antiseptic effect in an eye drop. For example, there is disclosed a method for inhibiting irritation of the eye due to pranoprofen by combination of an eye drop containing pranoprofen with tromethamine or 4-(2-hydroxyethyl)-1-(2-sulfoethyl)piperazine (see JP-A-8-291065 (U.S. Pat. No. 3,170,619)). Further, there is disclosed a method for improving antiseptic effect of sulfa drugs solubilization and by combination of an eye drop containing a sulfa drug with an alkanolamine such as monoethanolamine, diethanolamine, and triethanolamine, followed by dissolution (see JP-B-1-29170; JP-A-59-89616; JP-A-61-12617). There is also disclosed a diclofenac sodium eye drop combined with trometamol or its homolog of not more than 10 carbon atoms as antiseptic and stabilizer (see JP-A-62-242617; JP-A-62-242618).

However, in these prior literatures, there is no description indicating that intraocular penetration of 2-amino-3-(4-bromobenzoyl)phenylacetic acid or its pharmacologically acceptable salt or a hydrate thereof was promoted, and an effective concentration of 2-amino-3-(4-bromobenzoyl)phenylacetic acid was retained in the anterior aqueous humor for treating inflammatory diseases.

DISCLOSURE OF THE INVENTION

Problem to be Solved by the Invention

An object of the present invention is to provide an aqueous eye drop which is administered once a day, comprising, as an active ingredient, an anti-inflammatory 2-amino-3-(4-bromobenzoyl)phenylacetic acid or its pharmacologically acceptable salt thereof or a hydrate thereof and having a promoted intraocular penetration and a prolonged retention time of an effective concentration of 2-amino-3-(4-bromobenzoyl)phenylacetic acid penetrated into the anterior aqueous humor for treating inflammatory diseases.

Means for Solving the Problem

As a result of intensive studies for achieving the above object, the present inventors have found that an aqueous eye drop, which is obtained by combination of 2-amino-3-(4-bromobenzoyl) phenylacetic acid or its pharmacologically acceptable salt or a hydrate thereof with an organic amine or a salt thereof, is administered once a day, thereby to promote the penetration of 2-amino-3-(4-bromobenzoyl)phenylacetic acid into the ocular tissue and retain a therapeutically effective concentration of said compound in the anterior aqueous humor over a period of at least 24 hours after the administration. Thus, the present inventors have achieved the completion of the present invention.

That is to say, the present invention provides the following methods:

(1) a method for treating inflammatory diseases of the external segment or the anterior segment of the eyes, which comprises administering an aqueous eye drop comprising 2-amino-3-(4-bromobenzoyl) phenylacetic acid or its pharmacologically acceptable salt or a hydrate thereof once a day, and maintaining a therapeutically effective concentration of 2-amino-3-(4-bromobenzoyl) phenylacetic acid in the anterior aqueous humor at least for 24 hours after the administration, (2) the method according to the above (1), wherein the aqueous eye drop comprising 2-amino-3-(4-bromobenzoyl) phenylacetic acid or its pharmacologically acceptable salt or a hydrate thereof comprises an organic amine or a salt thereof, and the content of the aforementioned organic amine or salt thereof is an amount to allow the octanol-water partition coefficient of 2-amino-3-(4-bromobenzoyl)phenylacetic acid to be 0.7 to 4, (3) the method according to the above (1) or (2), wherein the concentration of 2-amino-3-(4-bromobenzoyl)phenylacetic acid or its pharmacologically acceptable salt or a hydrate thereof in the aqueous eye drop is 0.01 to 0.5 w/v %, (4) the method according to the above (2), wherein the organic amine is at least one member selected from the group consisting of an amino acid, an alkanolamine, a diamine, a piperazine, and an aminoalkylsulfonic acid, (5) the method according to the above (2) or (4), wherein the organic amine is an amino acids and its concentration is 0.35 to 5 w/v %, (6) the method according to the above (2) or (4), wherein the organic amine is an alkanolamine and its concentration is 0.15 to 0.95 w/v %, (7) the method according to the above (6), wherein the alkanolamine is trometamol, (8) the method according to the above (2) or (4), wherein the organic amine is a diamine and its concentration is 0.05 to 5 w/v %, (9) the method according to the above (2) or (4), wherein the organic amine is a piperazine and it is contained at a concentration of 0.05 to 5 w/v % in the aqueous eye drop,

(10) the method according to the above (2) or (4), wherein the organic amine is an aminoalkylsulfonic acid and its concentration is 0.05 to 5 w/v %,

(11) the method according to the above (10), wherein the aminoalkylsulfonic acid is aminoethylsulfonic acid, and

(12) a method for promoting intraocular penetration of 2-amino-3-(4-bromobenzoyl)phenylacetic acid or its pharmacologically acceptable salt or a hydrate thereof, which comprises administering an aqueous eye drop comprising 2-amino-3-(4-bromobenzoyl)phenylacetic acid or its pharmacologically acceptable salt or a hydrate thereof comprises an organic amine or a salt thereof, wherein the content of said organic amine or salt thereof is an amount to allow the octanol-water partition coefficient of 2-amino-3-(4-bromobenzoyl)phenylacetic acid to be 0.7 to 4.

In addition, the present invention provides the following inventions:

(13) an aqueous eye drop for once a day administration for treating inflammatory diseases of the external segment or the anterior segment of the eyes, characterized in that a therapeutically effective concentration of 2-amino-3-(4-bromobenzoyl)phenylacetic acid or its pharmacologically acceptable salt or a hydrate thereof is maintained in the anterior aqueous humor for at least 24 hours by once a day administration,

(14) the aqueous eye drop according to the above (13), wherein the concentration of 2-amino-3-(4-bromobenzoyl) phenylacetic acid or its pharmacologically acceptable salt or a hydrate thereof in the aqueous eye drop is 0.01 to 0.5 w/v %,

(15) the aqueous eye drop according to the above (13) or (14), wherein the aqueous eye drop comprising 2-amino-3-(4-bromobenzoyl)phenylacetic acid or its pharmacologically acceptable salt or a hydrate thereof comprises an organic amine or a salt thereof, and the content of said organic amine or salt thereof is an amount to allow the octanol-water partition coefficient of 2-amino-3-(4-bromobenzoyl)phenylacetic acid contained in the aqueous eye drop to be 0.7 to 4,

(16) the aqueous eye drop according to the above (15), wherein the organic amine is at least one member selected from the group consisting of an amino acid, an alkanolamine, a diamine, a piperazine, and an aminoalkylsulfonic acid,

(17) the aqueous eye drop according to the above (15) or (16), wherein the organic amine is an amino acid and its concentration is 0.35 to 5 w/v %,

(18) the aqueous eye drop according to the above (15) or (16), wherein the organic amine is an alkanolamine and its concentration is 0.15 to 0.95 w/v %,

(19) the aqueous eye drop according to the above (18), wherein the alkanolamine is trometamol,

(20) the aqueous eye drop according to the above (15) or (16), wherein the organic amine is a diamine and its concentration is 0.05 to 5 w/v %,

(21) the aqueous eye drop according to the above (15) or (16), wherein the organic amine is piperazines and it is contained at a concentration of 0.05 to 5 w/v % in the aqueous eye drop,

(22) the aqueous eye drop according to the above (15) or (16), wherein the organic amine is an aminoalkylsulfonic acid and its concentration is 0.05 to 5 w/v %,

(23) the aqueous eye drop according to the above (22), wherein the aminoalkylsulfonic acid is aminoethylsulfonic acid, and

(24) an aqueous eye drop for once a day administration for treating inflammatory diseases of the external segment or the anterior segment of the eyes, characterized in that a therapeutically effective concentration of 2-amino-3-(4-bromobenzoyl)phenylacetic acid is maintained in the anterior aqueous humor for at least 24 hours by once a day administration of 0.01 to 0.5 w/v % 2-amino-3-(4-bromobenzoyl)phenylacetic acid or its pharmacologically acceptable salt or a hydrate thereof and 0.05 to 5 w/v % aminoethylsulfonic acid.

Further, the present invention provides the following inventions:

(25) use of an organic amine or its salt for producing an aqueous eye drop which is to be administered once a day, characterized in that the aqueous eye drop comprising 2-amino-3-(4-bromobenzoyl)phenylacetic acid or its pharmacologically acceptable salt or a hydrate thereof is administered once a day, and a therapeutically effective concentration of 2-amino-3-(4-bromobenzoyl)phenylacetic acid is maintained in the anterior aqueous humor for at least 24 hours by once a day administration to treat inflammatory diseases of the external segment or the anterior segment of the eyes,

(26) the use according to the above (25), wherein the concentration of 2-amino-3-(4-bromobenzoyl)phenylacetic acid or its pharmacologically acceptable salt thereof or a hydrate thereof in the aqueous eye drop is 0.01 to 0.5 w/v %,

(27) the use according to the above (25) or (26), wherein the amount of the organic amine or its salt used is an amount to allow the octanol-water partition coefficient of 2-amino-3-(4-bromobenzoyl)phenylacetic acid to be 0.7 to 4,

(28) the use according to the above (27), wherein the organic amine is at least one member selected from the group consisting of an amino acid, an alkanolamine, a diamine, a piperazine, and an aminoalkylsulfonic acid,

(29) the use according to the above (27) or (28), wherein the organic amine is an amino acid and its concentration is 0.35 to 5 w/v %,

(30) the use according to the above (27) or (28), wherein the organic amine is an alkanolamine and its concentration is 0.15 to 0.95 w/v %,

(31) the use according to the above (30), wherein the alkanolamine is trometamol,

(32) the use according to the above (27) or (28), wherein the organic amine is a diamine and its concentration is 0.05 to 5 w/v %,

(33) the use according to the above (27) or (28), wherein the organic amine is a piperazine and it is contained at a concentration of 0.05 to 5 w/v % in the aqueous eye drop,

(34) the use according to the above, (27) or (28), wherein the organic amine is an aminoalkylsulfonic acid and its concentration is 0.05 to 5 w/v %, and

(35) the use according to the above (34), wherein the aminoalkylsulfonic acid is aminoethylsulfonic acid.

Effect of the Invention

According to the present invention, the aqueous eye drop of the present invention is only administered once a day, thereby to be able to retain a therapeutically effective concentration of 2-amino-3-(4-bromobenzoyl)phenylacetic acid in the anterior aqueous humor for at least 24 hours after the administration. Further, there can be provided an aqueous eye drop comprising 2-amino-3-(4-bromobenzoyl)phenylacetic acid or its pharmacologically acceptable salt or a hydrate thereof, wherein an organic amine or its salt is combined to thereby promote intraocular penetration of 2-amino-3-(4-bromobenzoyl)phenylacetic acid or its pharmacologically acceptable salt or a hydrate thereof after administration of the eye drop, and retain a therapeutically effective concentration of 2-amino-3-(4-bromobenzoyl)phenylacetic acid for treating inflammatory diseases.

Therefore, the aqueous eye drop of the present invention can be advantageously used for treating, for example, uveitis, blepharitis, conjunctivitis, scleritis, postoperative inflammation or the like in the form of an eye drop which is administered once a day.

BEST MODE FOR CARRYING OUT THE INVENTION

Examples of pharmacologically acceptable salts of 2-amino-3-(4-bromobenzoyl)phenylacetic acid used in the aqueous eye drop of the present invention include, though not particularly limited, for example, an alkali metal salt such as sodium salt and potassium salt, an alkaline earth metal salt such as calcium salt and magnesium salt, and the like. Among these salts, a sodium salt is particularly preferable. 2-Amino-3-(4-bromobenzoyl)phenylacetic acid and its pharmacologically acceptable salt can be produced appropriately by the method according to JP-A-52-23052 (corresponding to U.S. Pat. No. 4,045,576) or its similar method. These compounds are obtained as hydrates thereof depending on the conditions such as synthesis and recrystallization. Examples of such hydrates include, though not particularly limited, for example, hemihydrates, monohydrates, and 3/2 hydrates, etc., among which 3/2 hydrates is particularly preferable.

With respect to the aqueous eye drop of the present invention, the content (concentration range) of 2-amino-3-(4-bromobenzoyl)phenylacetic acid or its pharmacologically acceptable salt or a hydrates is usually about 0.01 w/v % to 0.5 w/v %, preferably about 0.05 w/v % to 0.2 w/v %, particularly preferably about 0.1 w/v % to 0.2 w/v %. It is preferable to adjust the content appropriately according to the intended purpose and the degree of diseases to be treated.

In the aqueous eye drop of the present invention, an organic amine or its salt can be used in order to promote the penetration of 2-amino-3-(4-bromobenzoyl)phenylacetic acid or its pharmacologically acceptable salt or a hydrate thereof into the ocular tissue and to retain a therapeutically effective concentration of 2-amino-3-(4-bromobenzoyl)phenylacetic acid, which has been penetrated into the anterior chamber, in the anterior aqueous humor for at least 24 hours after the intraocular administration.

In the present invention, it is preferable to measure an octanol-water partition coefficient according to OECD Test Guideline 107 (adopted by the OECD Council "C (81) 30 Annex 1") or Japanese Industrial Standard Z7260-107 (2000) "Partition coefficient (1-octanol/water)-Shake flask method" and, to be more specific, such coefficient can be measured by the test method of Experimental Example 3 as described below.

In the present invention, as an organic amine or a salt thereof, preferred are those which are able to adjust a partition coefficient of 2-amino-3-(4-bromobenzoyl)phenylacetic acid to about 0.7 to 4 in the test method of Experimental Example 3 (Measurement of Octanol-Water Partition Coefficient) as described below. Examples of such organic amines or salts thereof include, for example, amino acids (e.g. arginine, histidine, aspartic acid, glutamic acid, serine, threonine, cysteine, phenylalanine, isoleucine, etc.), alkanolamines (e.g. monoethanolamine, diethanolamine, triethanolamine, trometamol, etc.), piperazines (e.g. HEPES (2-[4-(2-hydroxyethyl)-1-piperazinyl]ethanesulfonic acid), 1,4-bis(2-sulfoethyl)piperazine, etc.), diamines (e.g. ethylene diamine, trimethylene diamine, N,N'-bis(3-sulfopropyl)ethylene diamine, etc.), aminoalkylsulfonic acids (e.g. aminomethylsulfonic acid, aminoethylsulfonic acid, etc.) and the like. Among these amines, an alkanolamine or an aminoalkylsulfonic acid is preferable, and particularly preferred is aminoethylsulfonic acid or trometamol.

Examples of salts of an organic amine include inorganic acid salts (e.g. hydrochloride, nitrate, sulfate, sulfite, phosphate, or hydroiodide, etc.), organic acid salts (e.g. acetate, formate, oxalate, lactate, gluconate, adipate, or alkyl phosphate, etc.), inorganic base salts (e.g. sodium salt, calcium salt, magnesium salt, etc.), and organic base salts (e.g. ammonium salt, etc.).

These organic amines or salts thereof may be used solely or in combination of two or more salts.

In the aqueous eye drop of the present invention, it is preferable that the content (concentration range) of an organic amine or its salt is in the concentration range which allows a partition coefficient of 2-amino-3-(4-bromobenzoyl)phenylacetic acid to be about 0.7 to 4 in the test method of Experimental Example 3 (Measurement of Octanol-Water Partition Coefficient) as described below. Though the concentration range is different depending on a kind of the compound used and the like, the lower limit is usually about 0.01 w/v % and the upper limit is about 5.0 w/v %. For example, when an amino acid is used for the aqueous eye drop of the present invention, the lower limit of the content is about 0.35 w/v %, preferably about 0.4 w/v %, and the upper limit of the content is about 5 w/v %, preferably about 2 w/v %. When an alkanolamine is used, the lower limit of the content is about 0.15 w/v %, preferably about 0.2 w/v %, and the upper limit of the content is about 0.95 w/v %, preferably about 0.9 w/v %. When a diamine is used, the lower limit of the content is about 0.05 w/v %, preferably about 0.1 w/v %, and the upper limit of the content is about 5 w/v %, preferably about 2 w/v %. When a piperazine is used, the lower limit of the content is about 0.0.5 w/v %, preferably about 0.1 w/v %, and the upper limit of the content is about 5 w/v %, preferably about 2 w/v %. When an aminoalkylsulfonic acid is used, the lower limit of the content is about 0.05 w/v %, preferably about 0.1 w/v %, and the upper limit of the content is about 5 w/v %, preferably about 2 w/v %, more preferably about 1 w/v %. To be more specific, particularly, when an aminoethylsulfonic acid is used, the lower limit of the content is about 0.05 w/v %, preferably about 0.1 w/v %, and the upper limit of the content is about 5 w/v %, preferably about 2 w/v %, more preferably about 1 w/v %. When trometamol is used, the lower limit of the content is about 0.15 w/v %, preferably about 0.2 w/v %, and the upper limit of the content is about 0.95 w/v %, preferably about 0.9 w/v %.

The aqueous eye drop of the present invention is usually adjusted to the pH of about 5.0 to 9.0, preferably about 6.5 to 8.5, more preferably about 7.0 to 8.0.

In the preparation of the aqueous eye drop of the present invention, there may be appropriately added an additive usually used for eye drops, including, for example, isotonic agents (e.g. sodium chloride, potassium chloride, glycerin, concentrated glycerin, mannitol, sorbitol, boric acid, glucose, and propylene glycol, etc.), buffers (e.g. phosphate buffer, acetate buffer, borate buffer, carbonate buffer, citrate buffer, Tris buffer, glutamic acid, and ε-aminocaproic acid, etc.), water-soluble polymers (e.g. povidones (povidone K30 and povidone K25, etc.), polyvinyl alcohol, and sodium polyacrylate, etc.), surfactants (e.g. alkyl aryl polyether alcohol type polymers (e.g. tyloxapol, etc.), polyethylene glycol fatty acid esters (e.g. polyethylene glycol monostearate, etc.), polysorbate 80, polyoxyethylene hydrogenated caster oil, etc.), preservatives (e.g. benzalkonium chloride, benzethonium chloride, chlorhexidine gluconate, chlorobutanol, benzyl alcohol, sodium dehydroacetate, parahydroxybenzoic acid esters, disodium edetate, and boric acid, etc.), stabilizers (e.g. sodium bisulfite, sodium thiosulfate, disodium edetate, sodium citrate, ascorbic acid, and dibutylhydroxytoluene, etc.), and the like.

The amount of the additive may, though it is different depending on the kind and use, etc. of the additive to be added, be a concentration capable of accomplishing the intended use thereof. The isotonic agent can be usually added in an amount so as to give an osmotic pressure ratio of about 0.8 to 1.2. Further, it is preferable that the buffer is added in an amount of about 0.01 to 2 w/v %, the water-soluble polymer is added in an amount of about 0.1 to 10 w/v %, the surfactant is added in an amount of about 0.01 to 0.5 w/v %, the preservatives is added in an amount of about 0.0005 to 0.5 w/v %, and the stabilizer is added in an amount of about 0.001 to 1 w/v %.

The same or different kind of other active ingredients may be appropriately added to the aqueous eye drop of the present invention, unless they are contrary to the purpose of the present invention.

Examples of the same kind of active ingredients include, though not limited thereto, for example, pranoprofen, fluorometholone, prednisolone acetate, dexamethasone, and sodium azulene sulfonate, etc. Examples of the different kind of active ingredients include, for example, antimicrobial ingredients (e.g. ofloxacin, gatifloxacin, levofloxacin, ofloxacin, garenoxacin mesilate, pazufloxacin mesilate, tosufloxacin tosilate, norfloxacin, levofloxacin, lomefloxacin hydrochloride, cefmenoxime hydrochloride, chloramphenicol, sulfisoxazole, sulbenicillin sodium, tobramycin, and pimaricin, etc.), antiallergic ingredients (e.g. ketotifen fumarate, sodium cromoglycate, levocabastine hydrochloride, pemirolast potassium, chlorpheniramine maleate, ibudilast, and diclofenac sodium, etc.), active ingredients for treating corneal diseases (e.g. hyaluronic acid and salts thereof, etc.), antiglaucoma ingredients (e.g. timolol maleate, dipivefrine hydrochloride, bunazosin hydrochloride, isopropyl unoprostone, levobunolol hydrochloride, carteolol hydrochloride, pilocarpine hydrochloride, phenylephrine hydrochloride, tropicamide, and latanoprost, etc.), anticataract ingredients (e.g. pirenoxine, etc.).

The aqueous eye drop of the present invention can be produced according to the known method, for example, the method as described in Japanese Pharmacopoeia Fourteenth Edition, General Rules for Preparations, for example, the method by dissolving the above ingredients in an aqueous medium. Examples of such aqueous medium used include, for example, purified water, water for injection, and sterile purified water, etc.

The aqueous eye drop of the present invention can also be provided as an eye drop without no preservative (disposable type). With respect to the disposable eye drop, a single dose thereof is preferably stored in a tightly sealed container which can be opened at the time of use. In the case that the aqueous eye drop of the present invention is a disposable eye drop, there can be produced an eye drop which has no fear of contamination by microbes even if preservatives are not contained therein.

The present invention provides a method for prolonging a retention time of a therapeutically effective concentration of 2-amino-3-(4-bromobenzoyl)phenylacetic acid in the ocular tissue, particularly, in the anterior chamber or anterior ocular segment, characterized by intraocular administration of the above aqueous eye drop.

The therapeutically effective concentration of 2-amino-3-(4-bromobenzoyl)phenylacetic acid according to the present invention means a concentration at which an intraocular inflammation after anterior chamber puncture in rabbits can be inhibited by at least not less than about 25% as shown in Experimental Example 2 (Medicinal Efficacy Test in a Rabbit Model of Anterior Chamber Puncture) described below. The concentration at which the intraocular inflammation can be inhibited by at least not less than about 25% after anterior chamber puncture in rabbits is not less than about 1.5 ng/mL. The concentration of said medicament in the anterior chamber can be measured by the HPLC method for the anterior aqueous humor collected through anterior chamber puncture, as shown in Experimental Example 1 (Penetration Test of a Medicament in the Aqueous Humor) described below.

The aqueous eye drop of the present invention can prolong a retention time of therapeutically effective concentration of 2-amino-3-(4-bromobenzoyl)phenylacetic acid in the ocular tissue, particularly, in the anterior chamber or anterior ocular segment. The said prolongation of the retention time of the therapeutically effective concentration means that the retention time of the therapeutically effective concentration in the aqueous humor can last more than about 12 hours, preferably at least about 24 hours in the case where an eye drop containing 2-amino-3-(4-bromobenzoyl)phenylacetic acid or a salt thereof is administered once.

Since the aqueous eye drop of the present invention can retain the therapeutically effective concentration of 2-amino-3-(4-bromobenzoyl)phenylacetic acid for at least 24 hours after intraocular administration in the ocular tissue or anterior ocular segment, administration frequency of said aqueous eye drop can be once a day.

The doses of the aqueous eye drop of the present invention may be one to several (2 to 5) drops, and the dose frequency of said aqueous eye drop can be once a day for adults, for example, in the case where the eye drop of the present invention containing 0.1 w/v % of 2-amino-3-(4-bromobenzoyl)phenylacetic acid 3/2 hydrate is used for treating blepharitis, conjunctivitis, scleritis, postoperative inflammation, or uveitis, etc. In addition, the dose frequency of the eye drop can be appropriately increased or decreased depending on the symptom.

EXAMPLES

The present invention is further explained by the following Experimental Examples and Formulation Examples, but not limited thereto.

Experimental Example 1

Penetration Test into the Aqueous Humor

A penetration test of sodium 2-amino-3-(4-bromobenzoyl)phenylacetate of the following formulations (Table 1) into the aqueous humor was carried out using trometamol and aminoethylsulfonic acid.

1. Test Material

The eye drops of Formulations 1 to 3 in Table 1 were prepared and used.

TABLE 1

| Component | Formulation 1 | Formulation 2 | Formulation 3 |
|---|---|---|---|
| Sodium 2-amino-3-(4-bromobenzoyl)phenyl acetate 3/2 hydrate | 0.1 g | 0.1 g | 0.1 g |
| Boric acid | 1.8 g | — | — |
| Trometamol | — | 0.5 g | — |
| Aminoethylsulfonic acid | — | — | 0.2 g |
| Concentrated glycerin | — | 2.0 g | 2.4 g |
| Sodium hydroxide | q.s. | — | q.s. |
| Hydrochloric acid | — | q.s. | — |
| Purified water | q.s. | q.s. | q.s. |
| Total amount | 100 mL | 100 mL | 100 mL |
| pH | 7.8 | 7.8 | 7.8 |

2. Test Method

Rabbits (KITAYAMA LASES Co., Ltd) which have no abnormal cornea were selected (n=5), and 50 µL of each test material (eye drops of Formulations 1 to 3) was administered once to the rabbits by using a pipette. The rabbits were euthanized by overdosing a solution of pentobarbital sodium 2 hours after the intraocular administration. After the external segment of the eye was washed with physiological saline, the aqueous humor was collected by using a syringe with a 27G injection needle. 160 µL of the collected aqueous humor was mixed with 160 µL of a mobile phase for pretreatment/concentration as mentioned below, and then the mixture was filtered with a membrane filter (0.45 µm). The filtrate was served as a sample of HPLC measurement and then the concentration of 2-amino-3-(4-bromobenzoyl)phenylacetic acid was determined under the HPLC condition mentioned below by using High Performance Liquid Chromatograph (Shiseido Co., Ltd., type: Nanospace SI-1).

<HPLC Condition>

Detector: Ultraviolet spectrophotometer (wave length for measurement: 266 nm)

Column: (for pretreatment) Capcell pak MF Ph, 4.0×20 mm (Shiseido Co., Ltd.)

Column: (for concentration) Capcell pak C18 MG S5 mm 1.5×35 mm (Shiseido Co., Ltd.)

Column: (for analysis) Capcell pak C18 MG S5 mm 1.5×250 mm (Shiseido Co., Ltd.)

Column temperature: a constant temperature around 40° C., room temperature only for concentration column Mobile phase: (for pretreatment and concentration) phosphate buffer (pH 7.3)*: acetonitrile=90:10 (v/v)

Mobile phase: (for analysis) phosphate buffer (pH 7.3)*: acetonitrile=60:35 (v/v)

Injection amount: 70 µL×2=140 µL

* Phosphate buffer (pH 7.3): 50 mM diammonium hydrogenphosphate buffer (pH 7.3) containing 5 mM tetrabutylammonium chloride

TABLE 2

| Pump and valve switching schedule | | | | |
|---|---|---|---|---|
| Pump for analysis | | Pump for pretreatment and concentration | | Valve |
| Time(min) | Flow rate (mL/min) | Time (min) | Flow rate (mL/min) | Valve position |
| 0.0 | 100 | 0.0 | 500 | A |
| ↓ | ↓ | 0.5 | 250 | B |
| ↓ | ↓ | 5.5 | 10 | A |
| ↓ | ↓ | 29.5 | 500 | A |
| 30.0 | 100 | 30.0 | 500 | A |

3. Results

With respect to the eye drop of Formulation 1 (no addition of an organic amine), the concentration of 2-amino-3-(4-bromobenzoyl)phenylacetic acid in the aqueous humor was 214±46 (ng/mL) 2 hours after the intraocular administration. On the other hand, with respect to the formulation containing trometamol (the eye drop of Formulation 2) and the formulation containing aminoethylsulfonic acid (the eye drop of Formulation 3), concentrations of 2-amino-3-(4-bromobenzoyl)phenylacetic acid in the aqueous humor were respectively 260±45 (ng/mL) and 350±123 (ng/mL) 2 hours after the intraocular administration (Table 3). The concentration of 2-amino-3-(4-bromobenzoyl)phenylacetic acid in the aqueous humor 2 hours after the intraocular administration increased about 1.2 times in case of the formulation containing trometamol and about 1.6 times in case of the formulation containing aminoethylsulfonic acid compared to the eye drop of Formulation 1.

TABLE 3

| | 2-Amino-3-(4-bromobenzoyl)phenylacetic acid (ng/mL) |
|---|---|
| Formulation 1 | 214 ± 46 |
| Formulation 2 | 260 ± 45 |
| Formulation 3 | 350 ± 123 |

As can be seen above, the penetration of 2-amino-3-(4-bromobenzoyl)phenylacetic acid into the aqueous humor was elucidated to significantly increase by the addition of trometamol and aminoethylsulfonic acid which are an organic amine.

Experimental Example 2

Medicinal Efficacy Test in a Model Rabbit of Anterior Chamber Puncture

1. Test Animal

Male Dutch rabbits (Biotech Co., Ltd) with a body weight of about 2 kg was bred and acclimatized under the condition that the temperature was 23±2° C. and the humidity was 55±10%. On the day of the test, the flare value of anterior chamber in the rabbits was determined by a laser flare cell meter (FC-1000, Kowa Company, Ltd.). The rabbits having a flare value of not more than 30 and no abnormality in general condition were selected and used for the test.

2. Test Material

The eye drops of Formulations 4 to 6 in Table 4 were prepared and used.

TABLE 4

| Component | Formulation 4 | Formulation 5 | Formulation 6 |
|---|---|---|---|
| Sodium 2-amino-3-(4-bromobenzoyl)phenylacetate 3/2 hydrate | 0.1 g | 0.1 g | 0.1 g |
| Boric acid | 1.1 g | — | — |
| Borax | 1.1 g | — | — |
| Benzalkonium chloride | 0.005 g | — | — |
| Polysorbate 80 | 0.15 g | — | — |
| Povidone (K-30) | 2 g | — | — |
| Disodium edetate | 0.02 g | — | — |
| Sodium sulfite | 0.2 g | — | — |
| Sodium dihydrogenphosphate dihydrate | — | — | 0.05 g |
| Aminoethylsulfonic acid | — | 0.5 g | 1.0 g |
| Concentrated glycerin | — | 2.2 g | 2.6 g |
| Sodium hydroxide | q.s. | q.s. | q.s. |
| Purified water | q.s. | q.s. | q.s. |
| Total amount | 100 mL | 100 mL | 100 mL |
| pH | 8.3 | 7.8 | 7.0 |

3. Test Method

At 30 minutes before the puncture of the anterior chamber, 1,000 U/kg of heparin (Heparin sodium injection, Ajinomoto Co., Inc.) was administered into the rabbit's ear vein. A disposable intraocular injection needle (30G×3/4, Nipro Medical Industries, Ltd.) was curvedly punctured from the corneal center side at the position which is about 1 mm apart from the 1 o'clock position of rabbit's eyeball limbus to collect 80 μL of the anterior aqueous humor via the cornea (puncture of anterior chamber). The flare value (photon count/msec) in the anterior chamber was determined 30 minutes after the puncture of anterior chamber using a laser flare cell meter (FC-1000, Kowa Company, Ltd.). 50 μL of the test material was administered 24 hours before the puncture of anterior chamber. Meanwhile, nothing was administered to the control group.

An inhibition rate of inflammation after the puncture of anterior chamber was calculated according to the following equation.

Inhibition rate (%)=((Average flare value in the anterior chamber of the control group) minus (Average flare value in the anterior chamber of the test material administered group))/(Average flare value in the anterior chamber of the control group)×100

4. Results

Table 5 shows the inhibition rate of inflammation after the puncture of anterior chamber, which was calculated by the measured flare value in the anterior chamber. The inhibition rate of the formulation in which no aminosulfonic acid was added (Formulation 4) was 0.3% at 24 hours after the puncture. On the other hand, the inhibition rate of Formulation 5 was 25.5% and the inhibition rate of Formulation 6 was 73.9%, both of the formulations being combined with aminoethylsulfonic acid.

TABLE 5

| | Inhibition rate (%) |
|---|---|
| Formulation 4 | 0.3 (n = 6) |
| Formulation 5 | 25.5 (n = 7) |
| Formulation 6 | 73.9 (n = 10) |

Experimental Example 3

Measurement of Octanol-Water Partition Coefficient

1. Test Method

Sodium 2-amino-3-(4-bromobenzoyl)phenylacetate 3/2 hydrate and an organic amine were dissolved in 10 mM sodium dihydrogenphosphate dihydrate buffer (pH 7.8) in such a manner that said hydrate became to be 0.1 w/v % and said amine became to be 0.1 w/v %, 0.5 w/v %, and 1 w/v %. 5 mL of this solution and 5 mL of water-saturated octanol were poured into 20 mL of a glass ampoule. The ampoule was sealed and shaken at 100 rpm and 25° C. for 18 hours. After shaking, the glass ampoule was allowed to stand at room temperature. The octanol phase (upper phase) and the aqueous phase (lower phase) were taken into glass tubes respectively, using a Pasteur pipette. Each of the phase taken was centrifuged for 10 minutes at 2000 rpm to separate the octanol phase and the aqueous phase completely. Each 1 mL of the separated octanol phase and aqueous phase was diluted with a diluent solvent (water/acetonitrile=50/50 (v/v)) to a precise volume of 50 mL, and served as a sample for HPLC. The concentration of 2-amino-3-(4-bromobenzoyl)phenylacetic acid in each phase was determined by high performance liquid chromatography (Shimadzu Co., type:LC-10AD). As a control, there was used a solution of only sodium 2-amino-3-(4-bromobenzoyl)phenylacetate 3/2 hydrate dissolved in 10 mM sodium dihydrogenphosphate dihydrate buffer (pH 7.8) so as to be 0.1 w/v %.

2. Quantitative Analysis by HPLC

Detector: Ultraviolet spectrophotometer (wave length for measurement: 266 nm)

Column: A column packed with 5 μm of octadecylsilyl silica gel for liquid chromatography was used, wherein the column is a stainless tube having about 4.6 mm of inner diameter and about 25 cm of length. (CAPCELL PAK C18, SG120 5 μm, 4.6 mm I.D.×250 mm, Shiseido Co., Ltd.)

Guard column: ODS 80TS (TOSOH Co.) was used.

Column temperature: a constant temperature of around 40° C.

Mobile phase: 1.98 g of diammonium hydrogenphosphate was dissolved in 750 mL of water. Phosphoric acid was added thereto to adjust the pH to 7.3, and 250 mL of acetonitrile was mixed therewith.

Flow rate: 1.1 mL/min

Injection amount: 10 μL

3. Calculation of Octanol-Water Partition Coefficient

The octanol-water partition coefficient was calculated by the following equation.

Octanol-water partition coefficient=(Concentration of 2-amino-3-(4-bromobenzoyl)phenylacetic acid in the octanol phase)/(Concentration of 2-amino-3-(4-bromobenzoyl)phenylacetic acid in the aqueous phase)

4. Test Results

The results are shown in Table 6. The octanol-water partition coefficient of 2-amino-3-(4-bromobenzoyl)phenylacetic acid to which an organic amine was added showed higher value in comparison with the control. The results of the present test and Experimental Examples 1 and 2 show that the intraocular penetration of 2-amino-3-(4-bromobenzoyl)phenylacetic acid is promoted when an organic amine is combined therewith in such a manner that the octanol-water partition coefficient of 2-amino-3-(4-bromobenzoyl)phenylacetic acid becomes to be not less than about 0.7. Further, the results show that the 2-amino-3-(4-bromobenzoyl)phenylacetic acid inhibits the inflammation of the anterior segment even 24 hours after the intraocular administration.

TABLE 6

| Organic amine | Octanol-water partition coefficient | | |
|---|---|---|---|
| | 0.1%* | 0.5%* | 1%* |
| L-histidine | 0.69 | 0.96 | 1.05 |
| L-aspartic acid | 0.68 | 1.12 | 1.31 |
| L-glutamic acid | 0.68 | 1.08 | 1.24 |
| L-serine | 0.64 | 0.74 | 0.79 |
| L-threonine | 0.71 | 0.75 | 0.78 |
| L-cysteine | 0.55 | 0.88 | 0.81 |
| L-isoleucine | 0.61 | 0.67 | 1.55 |
| Monoethanolamine | — | 2.59 | 4.07 |
| Diethanolamine | — | 1.67 | 2.32 |
| Triethanolamine | — | 1.03 | 1.18 |
| HEPES | — | 0.93 | 1.05 |
| Ethylene diamine | — | 2.83 | 3.50 |
| Trimethylene diamine | — | 1.89 | 2.07 |
| Aminoethylsulfonic acid | — | 0.73 | 0.78 |
| Trometamol | — | 1.40 | 1.81 |
| Control | 0.60 | | |

*Concentration of an organic amine added

Formulation Example 1

Aqueous Eye Drop

| Component | Quantity |
|---|---|
| Sodium 2-amino-3-(4-bromobenzoyl)phenylacetate 3/2 hydrate | 0.1 g |
| Aminoethylsulfonic acid | 0.2 g |
| Benzalkonium chloride | 0.005 g |
| Tyloxapol | 0.02 g |
| Povidone (K30) | 2.0 g |
| Disodium edetate | 0.02 g |
| Concentrated glycerin | 2.2 g |
| Sodium hydroxide | q.s. |
| Purified water | q.s. |
| Total amount | 100 mL |
| pH | 7.8 |

According to the usual method, the above components were mixed to prepare an aqueous eye drop.

Formulation Example 2

Aqueous Eye Drop

| Component | Quantity |
|---|---|
| Sodium 2-amino-3-(4-bromobenzoyl)phenylacetate 3/2 hydrate | 0.1 g |
| Aminoethylsulfonic acid | 0.5 g |
| Benzalkonium chloride | 0.005 g |
| Tyloxapol | 0.02 g |
| Povidone (K30) | 2.0 g |
| Disodium edetate | 0.02 g |
| Boric acid | 1.3 g |
| Borax | 0.74 g |
| Sodium hydroxide | q.s. |
| Purified water | q.s. |
| Total amount | 100 mL |
| pH | 7.8 |

According to the usual method, the above components were mixed to prepare an aqueous eye drop.

Formulation Example 3

Aqueous Eye Drop

| Component | Quantity |
|---|---|
| Sodium 2-amino-3-(4-bromobenzoyl)phenylacetate 3/2 hydrate | 0.1 g |
| Aminoethylsulfonic acid | 0.5 g |
| Benzalkonium chloride | 0.005 g |
| Tyloxapol | 0.2 g |
| Povidone (K30) | 1.0 g |
| Disodium edetate | 0.02 g |
| Boric acid | 1.8 g |
| Sodium hydroxide | q.s. |
| Purified water | q.s. |
| Total amount | 100 mL |
| pH | 7.3 |

According to the usual method, the above components were mixed to prepare an aqueous eye drop.

Formulation Example 4

Aqueous Eye Drop

| Component | Quantity |
| --- | --- |
| Sodium 2-amino-3-(4-bromobenzoyl)phenylacetate 3/2 hydrate | 0.1 g |
| Aminoethylsulfonic acid | 0.5 g |
| Benzalkonium chloride | 0.005 g |
| Tyloxapol | 0.2 g |
| Povidone (K30) | 1.0 g |
| Disodium edetate | 0.02 g |
| Propylene glycol | 1.6 g |
| Sodium hydroxide | q.s. |
| Purified water | q.s. |
| Total amount | 100 mL |
| pH | 8.3 |

According to the usual method, the above components were mixed to prepare an aqueous eye drop.

Formulation Example 5

Aqueous Eye Drop

| Component | Quantity |
| --- | --- |
| Sodium 2-amino-3-(4-bromobenzoyl)phenylacetate 3/2 hydrate | 0.1 g |
| Aminoethylsulfonic acid | 1.0 g |
| Methyl parahydroxybenzoate | 0.037 g |
| Propyl parahydroxybenzoate | 0.02 g |
| Sodium dihydrogenphosphate dihydrate | 0.05 g |
| Concentrated glycerin | 2.4 g |
| Sodium hydroxide | q.s. |
| Purified water | q.s. |
| Total amount | 100 mL |
| pH | 7.0 |

According to the usual method, the above components are mixed to prepare an aqueous eye drop.

Formulation Example 6

Aqueous Eye Drop

| Component | Quantity |
| --- | --- |
| Sodium 2-amino-3-(4-bromobenzoyl)phenylacetate 3/2 hydrate | 0.1 g |
| Trometamol | 0.2 g |
| Benzalkonium chloride | 0.005 g |
| Tyloxapol | 0.02 g |
| Povidone (K30) | 2.0 g |
| Disodium edetate | 0.02 g |
| Concentrated glycerin | 2.0 g |
| Hydrochloric acid | q.s. |
| Purified water | q.s. |
| Total amount | 100 mL |
| pH | 7.8 |

According to the usual method, the above components are mixed to prepare an aqueous eye drop.

Formulation Example 7

Aqueous Eye Drop

| Component | Quantity |
| --- | --- |
| Sodium 2-amino-3-(4-bromobenzoyl)phenylacetate 3/2 hydrate | 0.1 g |
| Trometamol | 0.5 g |
| Benzalkonium chloride | 0.005 g |
| Polyoxyl 40 stearate | 0.05 g |
| Povidone (K30) | 2.0 g |
| Disodium edetate | 0.02 g |
| Boric acid | 1.8 g |
| Hydrochloric acid | q.s. |
| Purified water | q.s. |
| Total amount | 100 mL |
| pH | 7.5 |

According to the usual method, the above components are mixed to prepare an aqueous eye drop.

Formulation Example 8

Aqueous Eye Drop

| Component | Quantity |
| --- | --- |
| Sodium 2-amino-3-(4-bromobenzoyl)phenylacetate 3/2 hydrate | 0.1 g |
| Trometamol | 0.9 g |
| Methyl parahydroxybenzoate | 0.037 g |
| Propyl parahydroxybenzoate | 0.02 g |
| Sodium dihydrogenphosphate dihydrate | 0.05 g |
| Concentrated glycerin | 2.4 g |
| Sodium hydroxide | q.s. |
| Purified water | q.s. |
| Total amount | 100 mL |
| pH | 7.0 |

According to the usual method, the above components are mixed to prepare an aqueous eye drop.

Formulation Example 9

Aqueous Eye Drop

| Component | Quantity |
|---|---|
| Sodium 2-amino-3-(4-bromobenzoyl)phenylacetate 3/2 hydrate | 0.1 g |
| L-aspartic acid | 1.0 g |
| Benzalkonium chloride | 0.005 g |
| Tyloxapol | 0.02 g |
| Povidone (K30) | 2.0 g |
| Disodium edetate | 0.02 g |
| Sodium dihydrogenphosphate dihydrate | 0.05 g |
| Concentrated glycerin | 2.6 g |
| Sodium hydroxide | q.s. |
| Purified water | q.s. |
| Total amount | 100 mL |
| pH | 7.3 |

According to the usual method, the above components are mixed to prepare an aqueous eye drop.

Formulation Example 10

Aqueous Eye Drop

| Component | Quantity |
|---|---|
| Sodium 2-amino-3-(4-bromobenzoyl)phenylacetate 3/2 hydrate | 0.1 g |
| Monoethanolamine | 0.5 g |
| Methyl parahydroxybenzoate | 0.037 g |
| Propyl parahydroxybenzoate | 0.02 g |
| Sodium dihydrogenphosphate dihydrate | 0.05 g |
| Concentrated glycerin | 2.4 g |
| Sodium hydroxide | q.s. |
| Purified water | q.s. |
| Total amount | 100 mL |
| pH | 7.0 |

According to the usual method, the above components are mixed to prepare an aqueous eye drop.

Formulation Example 11

Aqueous Eye Drop

| Component | Quantity |
|---|---|
| Sodium 2-amino-3-(4-bromobenzoyl)phenylacetate 3/2 hydrate | 0.1 g |
| Ethylene diamine | 1.0 g |
| Benzalkonium chloride | 0.005 g |
| Polyoxyl 40 stearate | 0.05 g |
| Concentrated glycerin | 2.2 g |
| Hydrochloric acid | q.s. |
| Purified water | q.s. |
| Total amount | 100 mL |
| pH | 7.5 |

According to the usual method, the above components are mixed to prepare an aqueous eye drop.

Formulation Example 12

Aqueous Eye Drop

| Component | Quantity |
|---|---|
| Sodium 2-amino-3-(4-bromobenzoyl)phenylacetate 3/2 hydrate | 0.1 g |
| Sodium dihydrogenphosphate dihydrate | 0.05 g |
| Concentrated glycerin | 2.6 g |
| Sodium hydroxide | q.s. |
| Purified water | q.s. |
| Total amount | 100 mL |
| pH | 7.0 |

According to the usual method, the above components are mixed to prepare an aqueous eye drop.

Formulation Example 13

Aqueous Eye Drop

| Component | Quantity |
|---|---|
| Sodium 2-amino-3-(4-bromobenzoyl)phenylacetate 3/2 hydrate | 0.1 g |
| Aminoethylsulfonic acid | 0.5 g |
| Concentrated glycerin | 2.2 g |
| Sodium hydroxide | q.s. |
| Purified water | q.s. |
| Total amount | 100 mL |
| pH | 7.8 |

According to the usual method, the above components are mixed to prepare a disposable aqueous eye drop.

Formulation Example 14

Aqueous Eye Drop

| Component | Quantity |
|---|---|
| Sodium 2-amino-3-(4-bromobenzoyl)phenylacetate 3/2 hydrate | 0.1 g |
| Aminoethylsulfonic acid | 1.0 g |
| Sodium dihydrogenphosphate dihydrate | 0.05 g |
| Benzalkonium chloride | 0.005 g |
| Tyloxapol | 0.2 g |
| Povidone (K30) | 1.0 g |
| Disodium edetate | 0.02 g |
| Concentrated glycerin | 2.0 g |
| Sodium hydroxide | q.s. |
| Purified water | q.s. |
| Total amount | 100 mL |
| pH | 7.8 |

According to the usual method, the above components are mixed to prepare an aqueous eye drop.

INDUSTRIAL APPLICABILITY

According to the present invention, there can be provided an aqueous eye drop which can promote an intraocular penetration of 2-amino-3-(4-bromobenzoyl)phenylacetic acid or its pharmacologically acceptable salt thereof or a hydrate thereof and can maintain a therapeutically effective concentration of 2-amino-3-(4-bromobenzoyl)phenylacetic acid in the anterior aqueous humor for at least 24 hours for treating inflammatory diseases after the intraocular administration, characterized in that an organic amine or its salt is combined with an aqueous eye drop comprising, as an active ingredient, 2-amino-3-(4-bromobenzoyl)phenylacetic acid or its pharmacologically acceptable salt or a hydrate thereof.

Therefore, the aqueous eye drop of the present invention is advantageously used for treating blepharitis, conjunctivas, scleritis, postoperative inflammation, and uveitis, etc. in the form of an eye drop which is administered once a day.

The invention claimed is:

1. A method for promoting intraocular penetration of 2-amino-3-(4-bromobenzoyl)phenylacetic acid or its pharmacologically acceptable salt or a hydrate thereof, which comprises administering an aqueous eye drop comprising 2-amino-3-(4-bromobenzoyl)phenylacetic acid or its pharmacologically acceptable salt or a hydrate thereof and an organic amine selected from the group consisting of aminoethylsulfonic acid and aminomethylsulfonic acid or a salt thereof, wherein the content of the organic amine or salt thereof is an amount to allow the octanol-water partition coefficient of 2-amino-3-(4-bromobenzoyl)phenylacetic acid to be 0.7 to 4.

2. The method according to claim 1, wherein the concentration of 2-amino-3-(4-bromobenzoyl)phenylacetic acid or its pharmacologically acceptable salt or a hydrate thereof in the aqueous eye drop is 0.01 to 0.5w/v %.

3. The method according to claim 1, wherein the organic amine or salt thereof has a concentration of 0.05 to 5w/v %.

4. The method according to claim 1, wherein the organic amine is aminoethylsulfonic acid.

* * * * *